United States Patent [19]

O'Donnell et al.

[11] Patent Number: 5,344,324

[45] Date of Patent: Sep. 6, 1994

[54] APPARATUS AND METHOD FOR TESTING HUMAN PERFORMANCE

[75] Inventors: Robert D. O'Donnell, Dayton, Ohio; Samuel L. Moise, Jr., Los Gatos, Calif.

[73] Assignee: Nova Scientific Corporation, Tarzana, Calif.

[21] Appl. No.: 914,772

[22] Filed: Jul. 15, 1992

[51] Int. Cl.$^5$ .............................................. G09B 19/00
[52] U.S. Cl. .................................... 434/258; 434/118; 434/219; 434/236; 128/745; 364/551.01; 340/576; 345/904; 273/454
[58] Field of Search ............... 434/219, 236, 247, 258, 434/362, 365; 128/419 R, 745; 364/413.01, 413.05, 551.01; 340/576; 273/440, 454; 345/157, 161, 162, 904

[56] References Cited

U.S. PATENT DOCUMENTS

| | | |
|---|---|---|
| 3,357,115 | 12/1967 | Kelley ................................ 434/258 |
| 3,390,397 | 6/1968 | Friedlander ..................... 434/236 X |
| 3,483,302 | 12/1969 | Ashkenas et al. . |
| 3,579,865 | 5/1971 | Walker ............................... 434/258 |
| 3,811,116 | 5/1974 | Takeuchi et al. . |
| 3,892,053 | 7/1975 | Booher ............................... 434/258 |
| 3,901,215 | 8/1975 | John . |
| 3,918,176 | 11/1975 | Abernethy, III et al. . |
| 4,006,539 | 2/1977 | Slomski . |
| 4,166,452 | 9/1979 | Generales, Jr. . |
| 4,325,697 | 4/1982 | Regan et al. ....................... 434/258 |
| 4,486,180 | 12/1984 | Riley . |
| 4,541,806 | 9/1985 | Zimmerman . |
| 4,671,772 | 6/1987 | Slade et al. . |
| 4,683,891 | 8/1987 | Cornellier et al. .................. 434/236 |
| 4,750,888 | 6/1988 | Allard et al. . |
| 4,770,636 | 9/1988 | Buschke ............................. 434/236 |
| 4,854,329 | 8/1989 | Walruff . |
| 4,978,303 | 12/1990 | Lampbell . |
| 4,983,125 | 1/1991 | Smith et al. . |
| 5,103,408 | 4/1992 | Greenberg et al. . |
| 5,169,319 | 12/1992 | Potocki ............................... 434/236 |

OTHER PUBLICATIONS

"A Manual Control Test for the Detection and Deterence of Impaired Drivers," by Anthony C. Stein, R. Wade Allen, Henry R. Jex (Presented at the 20th Annual Conference on Manual Control, NASA Ames Research Center, 12-14 Jun. 1984).

Primary Examiner—Richard J. Apley
Assistant Examiner—Joe H. Cheng
Attorney, Agent, or Firm—Biebel & French

[57] ABSTRACT

Method and apparatus for testing human performance by measuring ability to employ job-related skills in an environment requiring skill switching in the presence of a forced attention shift. A human operator is tested by use of a monitor display upon which are presented an alternating sequence of primary tasks requiring utilization of different skills. A keyboard and a joy-stick are disclosed for use in performing the tasks. A danger indicating icon is presented along with the primary task, and the operator is forced to respond to danger indications thereof by operating a switch which is provided for that purpose.

15 Claims, 9 Drawing Sheets

APPARATUS AND METHOD FOR TESTING HUMAN PERFORMANCE

FIELD OF THE INVENTION

The present invention relates to human performance testing. More particularly, the invention relates to a testing procedure for measuring an individual's ability to perform a range of jobs or activity and detecting an impairment thereof due to drug or alcohol consumption or other causes of performance degradation.

BACKGROUND OF THE INVENTION

Modern day workers are required to operate equipment which is becoming increasingly more sophisticated. Each new generation of equipment demands a higher degree of operator skill. Consequently human operators are being asked to perform with increased competency, under greater stress, and with a smaller margin of error than ever before. This is particularly true in occupations involving the operation of computerized heavy equipment, high speed vehicles and other semi-automatic man/machine systems. And while the contemporary work place requires maximum performance, employers are finding that many workers are performing below their capability, and in some cases in an unsafe manner due to impairment by alcohol and drugs as well as other causes.

Estimates of the contribution of drug or alcohol impairment to industrial accidents range as high 50%. Vigorous education programs to ensure a drug-free work place have been instituted. Random biotesting has been undertaken as a supplement to education programs, with mixed levels of success. The difficulty with biochemical tests is that they merely establish that something is in the blood or urine. They do not establish that the chemical is impairing the performance of the person who has been tested. For this reason, biochemical tests are subject to varying court challenges. A further problem with biochemical testing is that it is expensive and time consuming and consequently limited to use on a relatively infrequent basis. Recent developments in a number of areas have resulted in the suggestion that behavioral tests may be more job-relevant, less invasive, more cost efficient and most importantly, equally or more valid in detecting drug, alcohol, and other causes of impairment.

A need therefore exists for an efficient and reliable test which addresses performance degradation generally, regardless of the degradation cause. Such a test should evaluate performance ability relevant to job requirements and to past performance of the individual being tested. A test of that type could be administered to large numbers of persons on a relatively frequent basis and could be complemented by chemical testing where warranted by an observed performance impairment.

The prior art teaches a number of techniques for testing human performance ability. For example, Smith et al. U.S. Pat. No. 4,983,125 discloses a device for measuring the ability of a human operator to stabilize an inherently unstable system. The Smith et al. device requires an operator to maintain a marker within predetermined limits on a moving track. A training period is provided during which the operator learns how to control the marker. In the Smith et al. device the difficulty is automatically increased at a relatively fast rate until the operator approaches the limits of his ability.

Another prior art teaching is shown in Abernethy et al U.S. Pat. No. 3,918,176 which discloses an intoxication testing system including means for simultaneously producing a pair of varying displays. A person being tested, selectively operates a pair of actuators in an attempt to track targets in the two displays. An analyzer measures and records the tracking errors. The subject is also required to watch a light which is periodically energized and to respond by actuating a switch. The switch actuation time is combined with the measured tracking error to provide a measurement of the intoxication level of the person being tested.

Another prior art performance testing device is disclosed in Slomski U.S. Pat. No. 4,006,539. The Slomski device tests the alertness and perception speed of the subject. Slomski's equipment tests psycho-physiological functions, primarily responsiveness to a visual stimulation. The device emits flash signals at different locations and for different durations of time. The subject's reaction to the flashing lights is used as a measure of performance.

A further example of the prior art is shown in Ashkenas et al. U.S. Pat. No. 3,483,302 which discloses a performance testing system wherein the subject performs a tracking operation within a feedback loop having a variable gain. The system is inherently unstable, and the test effectively measures the operator's ability to stabilize the loop.

The prior art also includes a performance testing system as described in Greenberg et al, U.S. Pat. No. 5,103,408. That system tests attention allocation ability by displaying two tasks simultaneously on a monitor together with an arrow indicating which task is to be performed. One task requires the subject to determine the orientation of an object while the other requires recognition and memorization of an alphanumeric character. After the subject has performed one of the tasks, the monitor displays two more tasks along with another indicating arrow. A series of such displays are presented, and a score is assigned for each performance. The scores are combined and compared with scores achieved by the same individual in previous tests. It has been found that this test provides a fairly reliable indication of drug or alcohol impairment, but a still better performance test is required.

SUMMARY OF THE INVENTION

The present invention provides a fast and effective method and apparatus for measuring the ability of an individual to perform a multi-skill activity. The method is performed with the aid of a programmed computer, a visual display device (monitor) and appropriate operator input means. In accordance with the invention the operator (person to be tested) is seated in front of the monitor and is directed to perform two or more different tasks on an alternating basis. The two tasks are designed to require utilization of different types of operator skills. As the tasks are alternated, the operator is required to switch back and forth between the different skills.

Preferably at least one of the tasks is a cognitive task requiring the operator to process a plurality of different, cognitively relevant stimuli, each of which occurs in a plurality of different states. Preferably, the stimuli are presented according to a balanced regimen such that each of the stimuli appears in each of its states an equal number of times. The presentation is made according to a pseudorandom sequence, so that the operator may not anticipate the task parameters. The cognitive task may be presented on an alternate basis with a motor task or another cognitive task. However, each task may comprise different numbers of successive trials, the number of which varies according to a pseudorandom sequence, so that the operator may not anticipate the switch from the cognitive skill to the motor skill.

The system monitors and records the performance of the operator, and the data, so recorded, may be used to predict decrements in job performance. Such data also may be compared to past performance data and used as an indicator of alcohol, drug, or other impairment.

As an optional feature the computer may display a modifiable icon simultaneously with one or both of two primary tasks. The operator is required to observe this icon and to perform some designated act whenever the icon assumes a particular designated state. In the preferred embodiment the icon may comprise a dial having a position which is varied up and down on a stepwise basis. This optional feature may provide a further indication of drug, alcohol, or other impairment.

Thus, it is an object of the present invention to provide a fast and effective test for measuring the ability of an individual to perform a multi-skill activity.

It is another object of the present invention to provide an improved method and apparatus for detecting performance impairment due to drugs, alcohol, or other causes, by non-intrusive means.

Other objects and advantages of the present invention will be apparent from the following description, the accompanying drawings and the appended claims.

DESCRIPTION OF THE PREFERRED EMBODIMENT

Figure 1:
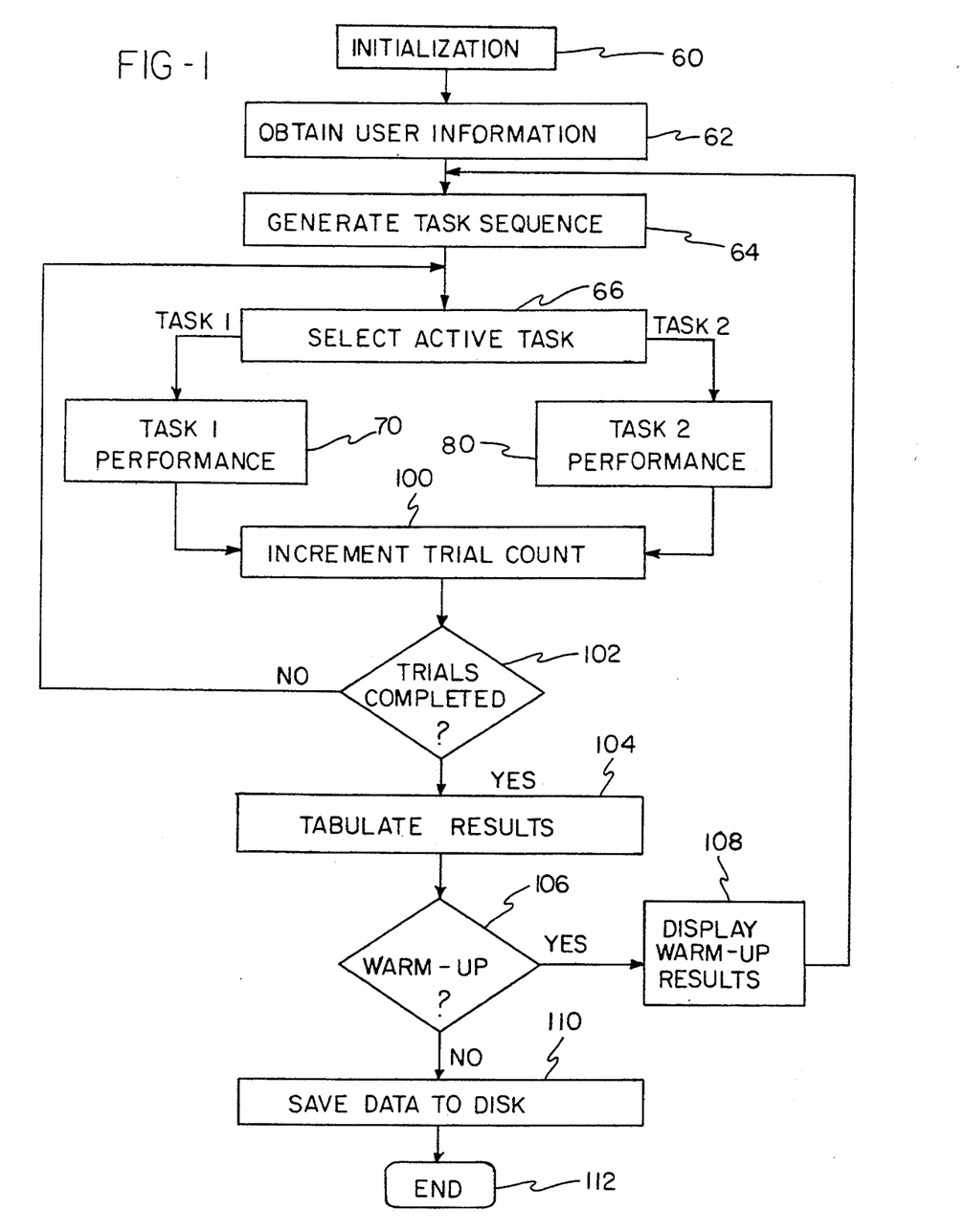
FIG. 1 is a flow chart of performance test using a switching skill paradigm.

The present invention provides a method and apparatus for testing the ability of an operator to engage in a wide variety of high-skill activities. The invention employs a skill switching paradigm wherein two or more different tasks are alternately presented to the operator. These tasks test the operator's ability to utilize particular skills and to switch between skills. Throughout the test the operator simultaneously monitors a dial which is subject to a change of position. This adds a forced attention shift. FIG. 1 presents a flow chart summarizing the operation of the invention.

Figure 7:
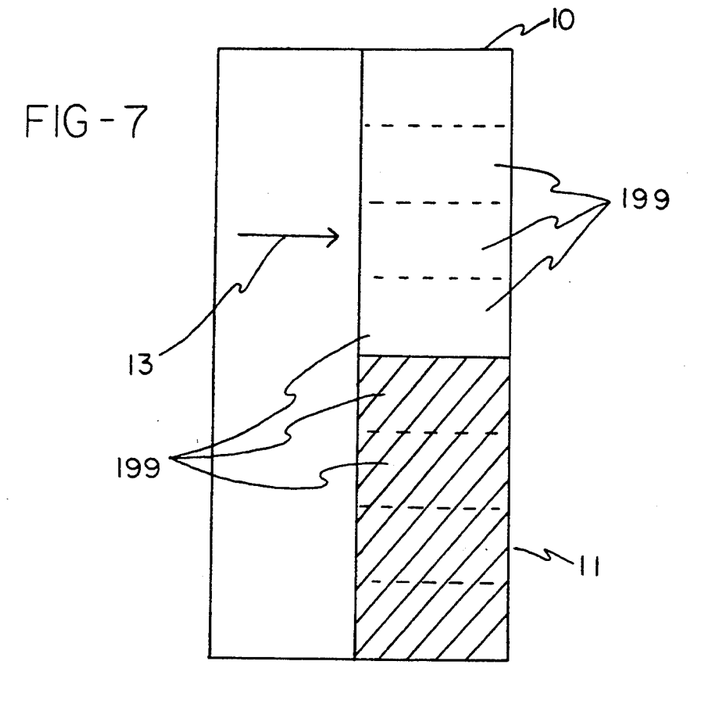
FIG. 7 is an enlarged illustration of a dial-type icon.
Figure 8:
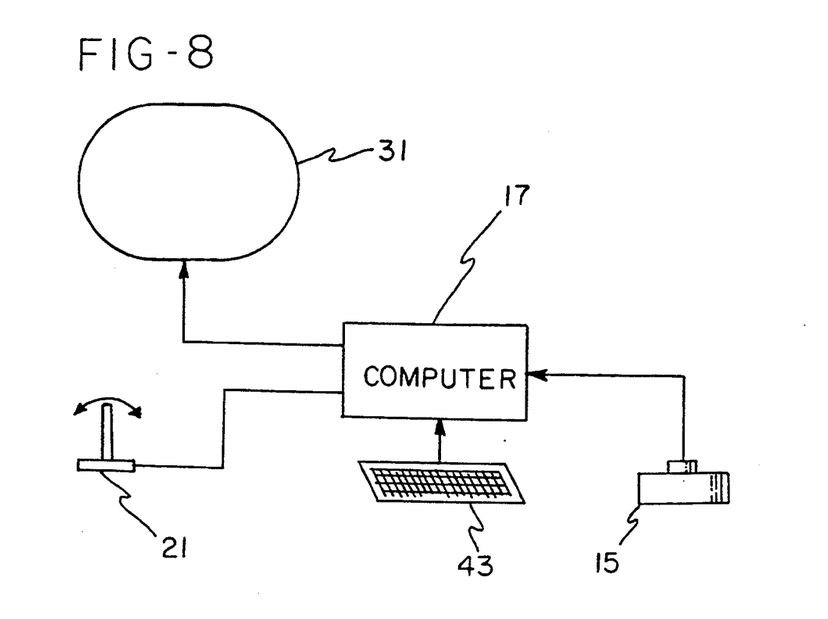
FIG. 8 is a schematic illustration of apparatus for practicing the invention.

The invention preferably employs a programmed personal computer 17 having a keyboard 43, as illustrated in FIG. 8. Computer 17 is connected to a display monitor 31 of a type having graphic capabilities. The system software causes the monitor to display the two different tasks on an alternating basis in combination with a modifiable icon dial (illustrated in detail in FIG. 7) which appears continuously in a corner of the display.

As shown in FIG. 1, the test sequence begins by initializing computer 17 (block 60 at FIG. 1). Once the computer has been initialized, the person administering the test enters information which identifies the individual being tested (block 62). The program then proceeds to block 64 for generation of sets of digital codes representing sequences of tasks, task graphics and dial positions to be presented on the display. These codes are loaded into tables for subsequent use in controlling task presentation and switching.

Figure 2A:
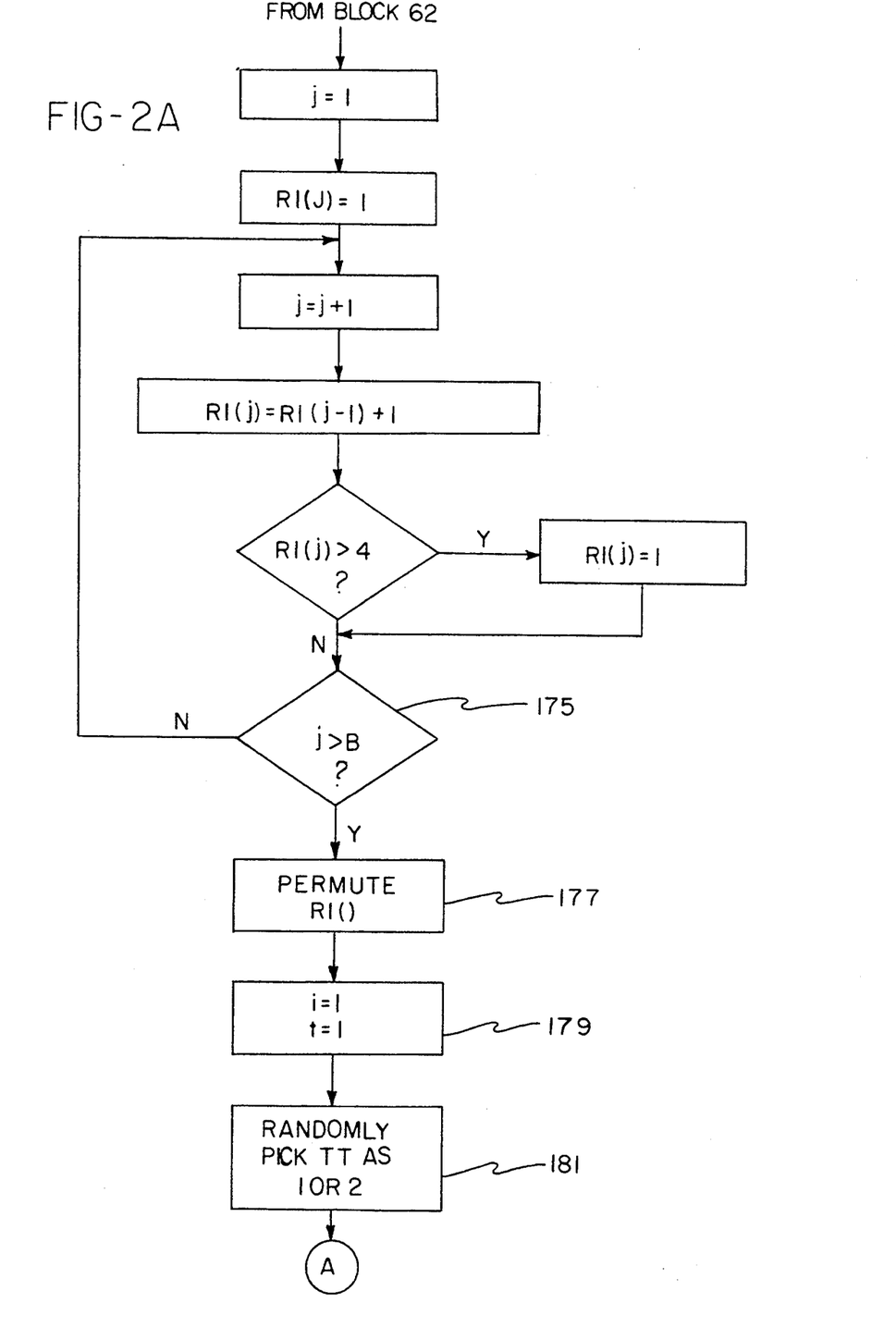
FIGS. 2A-2C are flow charts of a subroutine for task sequence generation.
Figure 2B:
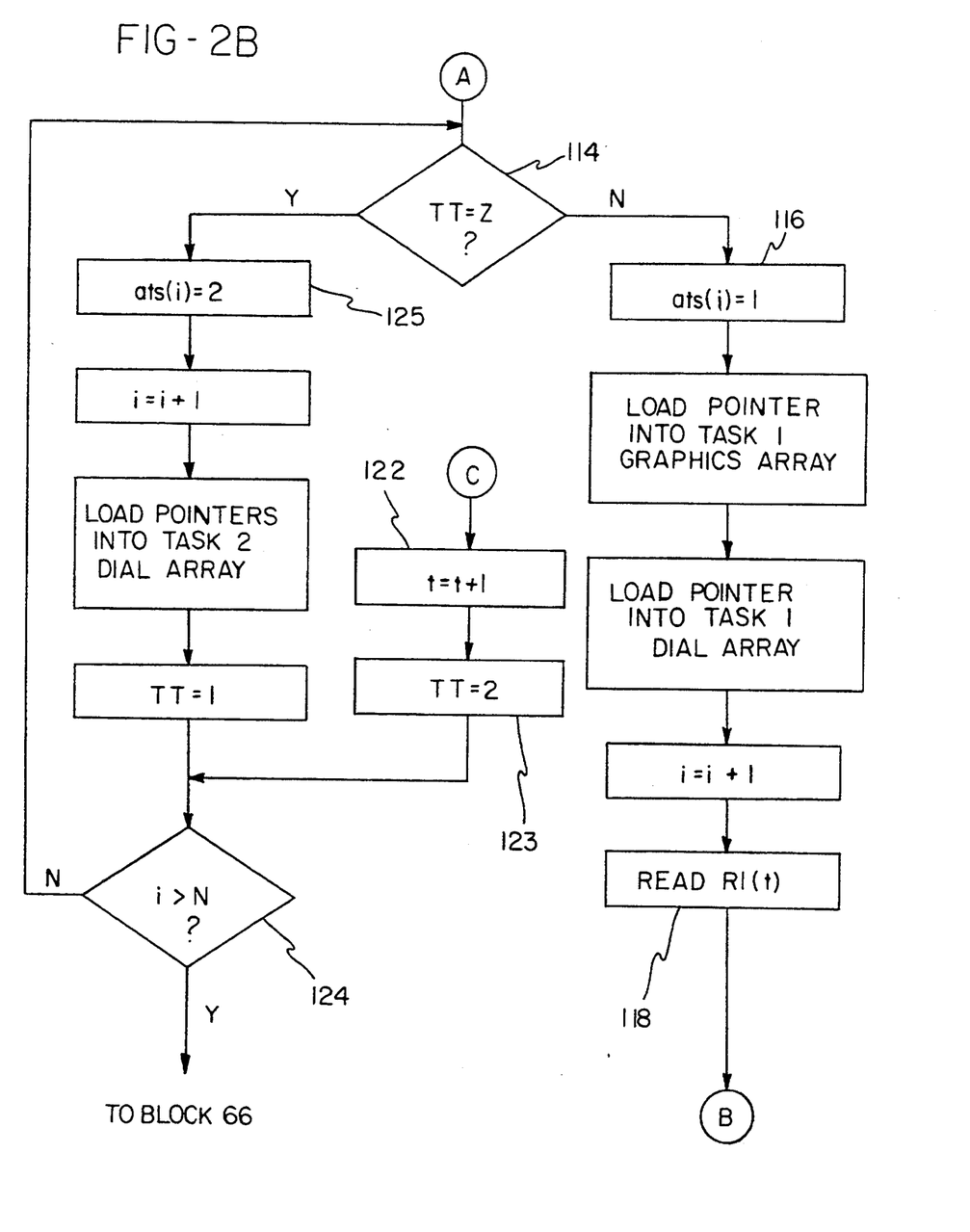
Figure 2C:
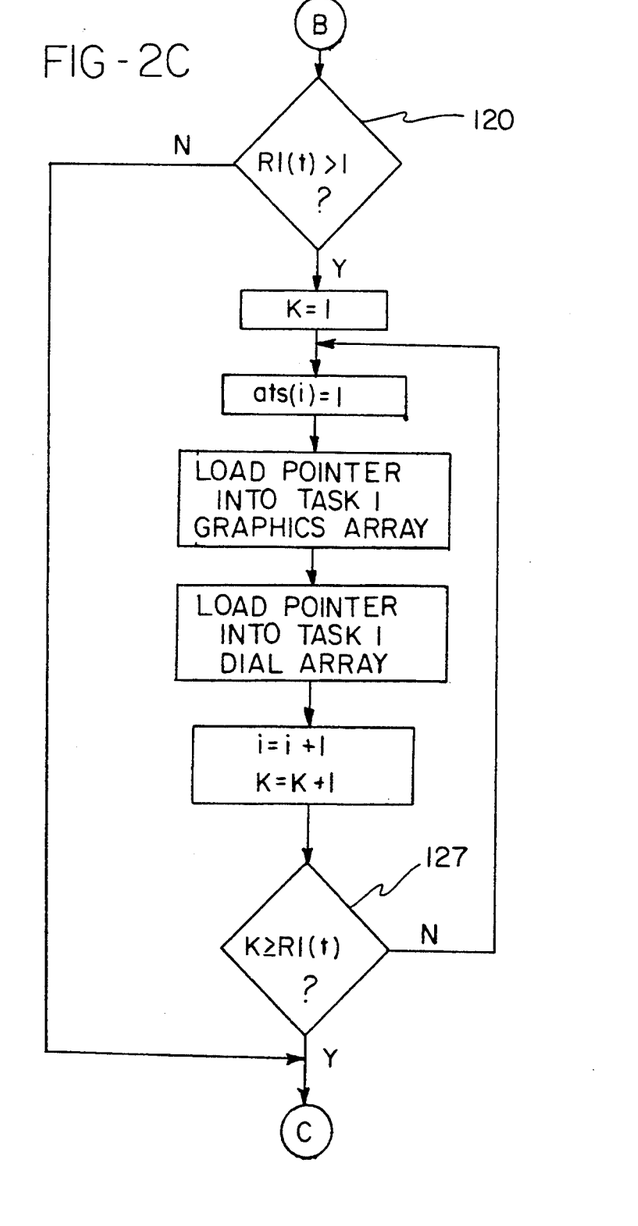

FIG. 2 presents a flow chart of a subroutine for generating a task sequence for a series of N trials. The program has a task designation array ats() filled with ones and twos to designate task numbers. During a task in accordance with this invention, the computer reads the values which are stored sequentially in the task designation array and switches back and forth between Task 1 and Task 2. The subroutine of FIGS. 2A thru 2C also loads values into a runs array R1(), the size of which is related to the number of psychologically significant parameters which may be varied during the course of a group of trials. It is a feature of this invention that the program balances the presentation of the various images by placing a predetermined sequence of pointers into a graphics control array and then permuting the array to produce a pseudorandom sequence of pointers. The runs array R1() is first filled, as illustrated in FIG. 2A, by varying a counter, as indicated by the reference character j from a value of 1 up through a value such as 32 which may represent the maximum number of image variations within the group of trials. As illustrated in FIG. 2A the runs array, R1(), is filled with eight sets of the number sequence 1 thru 4. At block 177 the runs array is permuted using a conventional algorithm to place the eight sets of numbers into a pseudorandom sequence. At the same time the program creates a pseudorandom sequence of pointers to the storage locations where the 32 different images are stored. The program then is ready to begin filling the task designation array, ats().

Filling of the task designation array begins at block 179 by setting a pair of counters indicated by the characters i and t. The program then proceeds to block 181 where it uses a conventional random number generating routine to pick a pseudorandom value of 1 or 2 for a variable indicated by the characters TT. The program then proceeds to point 114 (FIG. 2B) where it checks the value of TT. If TT is found to have a value of 2, then the program loads the value "2" into the ith location of the ats() array and increments the counter i. It then loads pointers from a pseudorandom sequence into the Task 2 dial array. After this the program toggles the value of TT from 2 to 1 and checks to find out whether the counter i exceeds the number of specified trials N. If so, then the program exits to block 66. Otherwise, there is a return to point 114.

If the check at point 114 indicates that TT does not have a value of 2, then the program proceeds to block 116 where ats(i) is set equal to 1. The program then reads pointer values from pseudorandom sequences into the Task 1 graphics array and the Task 1 dial array. The counter i is then incremented, and the program proceeds to block 118 where it reads the value at position t in the runs array. A check is then made at point 120 to determine whether the runs array value at that location is greater than 1. If not, (i.e. R1(t) equals 1) then the program proceeds to block 122 (FIG. 2B) where it increments the count in the t counter and toggles the variable TT to a value of 2 (block 123). If the counter i does not exceed the value N, then the program loops through point 124 back to point 114 and through block 125 at which a value of 2 is put into the next position in the task designation array.

If the check at point 120 indicates that the value at the t position in the runs array is greater than 1, then the program will begin looping through point 127. The number of loops is determined by the value of the runs array at position t. For each loop through point 127 the program will set a value of 1 into the task designation array and load pointers into the Task 1 graphics array and the Task 1 dial array. This will cause the test to generate from 1 to 4 consecutive occurrences of Task 1 and to present a balanced variation of Task 1 configurations on a pseudorandom basis. It is preferred that the tables generated by the subroutine of FIGS. 2A–2C cause the operator to be given a balanced presentation of cognitively relevant stimuli. This is done by calculating the total number of combinations of each of the stimuli in each of their states (the basic group, B) and presenting each combination an equal number of times. The variable B is used at point 175 to control the filling of the runs array. The balanced presentation is assured by a subroutine within block 62 (FIG. 1) which checks the value of N (number of trials) input by the test administrator. If N is not evenly divisible by the basic group number B, then the test administrator may be prompted to input a different number. Alternatively, the computer may use a substitute value of N obtained by calculating the nearest number which is evenly divisible by the basic group number B.

Again, referring to FIG. 1, after the task sequence has been established, the table of values in the task designation array is consulted and the first value therein is used for controlling the task type for the first task (block 66). For example, if the first value is 1, then the program may proceed to block 70 and perform the procedure for Task 1. A value of 2 may cause the program to branch to block 80 and perform the procedure for Task 2. The operator then performs the selected task, after which a trial counter (which was initialized at block 60) is incremented (block 100) and compared with the value of N (point 102). A new task is then selected, and the process is repeated until N trials have been completed. After all N trials have been completed, the results are tabulated (block 104). As illustrated in FIG. 1, the program can be run for warm-up trials prior to a record session. After N trials have been completed and the results tabulated, the program checks (at point 106) to determine whether the session was a warm-up run. If so, then the test results are displayed on the monitor (block 108). If it was not a warm-up session, then the data are saved to disk (block 110), so that they may be compared to the operator's baseline (established from prior performances) and used for baseline updating. The data are also available for immediate use by the test administrator. This ends the program (112).

If the results of the test deviate more than a predetermined amount from the operator's baseline scores, a second (or further) test session is performed. If the scores continue to deviate by more than a predetermined amount after this additional testing, then an alerting message is generated and a chemical test for drugs or alcohol may be appropriate. In any event, substandard test results provide an immediate indication of degraded performance ability and afford a basis for further inquiry regarding the operator's condition.

Figure 3:
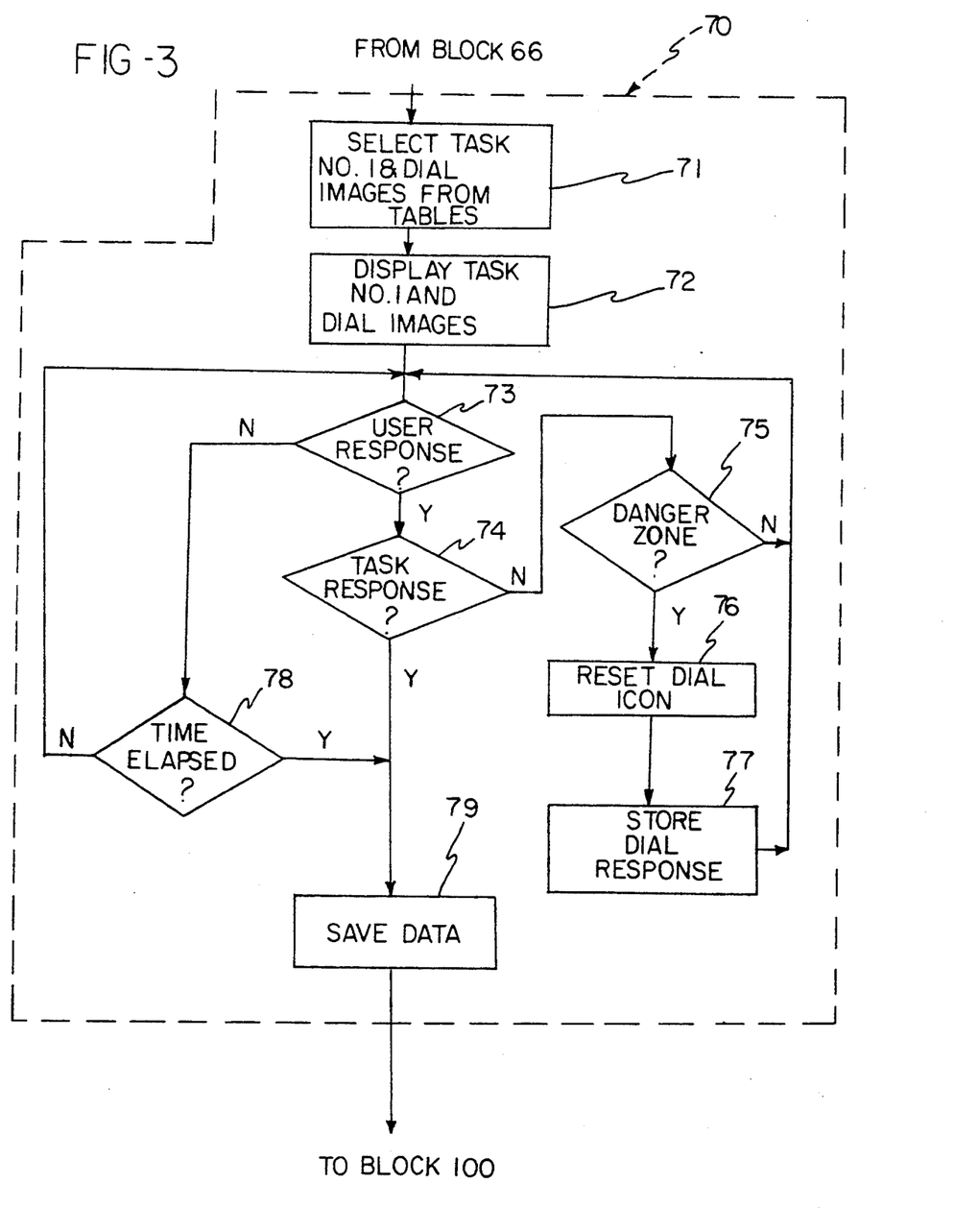
FIG. 3 is a flow chart of a routine for presenting a task requiring a cognitive skill.
Figure 5:
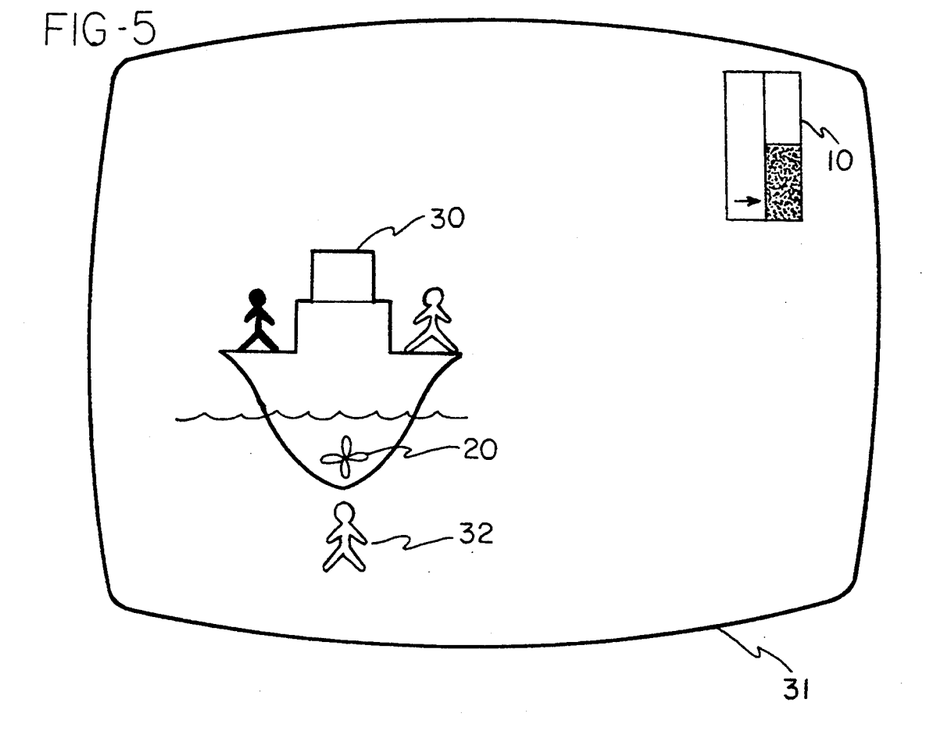
FIG. 5 is an illustration of a monitor display for a task requiring the use of a cognitive skill.

FIG. 3 shows the detailed steps generally encompassed by block 70 of FIG. 1. Thus the figure presents a flow chart for a task requiring the use of a cognitive skill. For explanatory purposes this task is referred to as Task 1. Selection of that task may cause a monitor display of the type illustrated in FIG. 5. This task may, for instance, exercise a skill related to visualization of spatially rotated objects by requiring the operator to recognize that the uncolored figure denoted by the reference numeral 32 corresponds to another uncolored figure on the starboard or right side of a departing and vertically upright ship 30 (propeller 20 indicates the stern of the ship). Having made this connection the operator should understand that he is to respond by pressing a designated key on the computer keyboard. Alternatively the program may present the display with no propeller or similar indication 20, in which case the ship would be approaching the operator, and the correct response would be a different designated key for left or port. It will be understood that the positions of the figures are also subject to variation. As illustrated, the cognitively relevant stimuli are the coloration state of the figures, the position of the reference figures, the direction of movement of the ship, the vertical orientation of the ship, and the condition of dial 10. Each of these stimuli has two possible states, so that the basic group has 32 possible combinations and the variable B has a value of 32. In any case the task must be performed within an allotted maximum period of time.

The dial or indicator-type icon 10 remains in the upper right-hand corner of the screen while monitor 31 is displaying the ship 30. The rules for the test require the operator to observe the icon 10 while he performs the primary task and to respond as discussed below. The program routine begins by reading the tables containing the image control codes for Task 1 and its associated dial presentation (block 71). These codes then are used at block 72 for generation of the actual images. The program then proceeds to point 73 where it checks for a keyboard input from the operator. It loops from point 73 to point 78 and back to point 73 while the operator ponders the problem presented by the display. The looping terminates when the operator depresses a switch 15 which is connected to an input port of computer 17 (FIG. 8) or either one of two designated task response keys. Switch 15 signals an order to reset the dial while the two designated keys indicate "port" or "starboard" responses. At point 78 an elapsed time check is made. If a predetermined time limit has been reached then the program branches to block 79 where the task data are saved, following which the program exits the task.

If an operator response is detected at point 73, then the program checks (at point 74) to determine whether the response is a "task" response. If so the response is recorded at block 79 and a task exit is executed. If the operator response is determined not to be a "task" response, then the program knows that a dial reset has been ordered. However, before resetting the dial, the program checks at point 75 to determine whether the dial is in the danger zone. If not, then the program records the inappropriate response and loops back to point 73 to look for another response. In the event that the dial is in the danger zone then the dial is reset to the safe zone at block 76. A record of the time of the response is stored at block 77, and, again, the program loops back to point 73.

The dial icon 10, as shown in detail in FIG. 7 is divided into 8 stacked segments 199, each segment being of equal height. The bottom 4 segments represent the above noted Danger Zone 11 which may be presented as a shaded area. A moving indicator 13 can point at any one of segments 199. The SAFE/DANGER combination of the dial icon is one of the cognitively relevant stimuli which are balanced by the test of this invention. Accordingly, the tables used for selection of the dial condition are loaded with numbers which will produce an equal number of occurrences of each state throughout the course of the Task 1 trials. Again, the table values are entered pseudorandomly to avoid anticipation of the stimulus state by the operator. Each dial state may be manifested by any one of 4 dial positions, also subject to pseudorandom presentation.

During a Task 1 trial the indicator is initially set to a fixed position and does not thereafter move, unless it appears in the Danger Zone and is reset by operator activation of switch 15. In that case the dial moves to a safe position and remains there throughout the remainder of the trial. During a Task 2 trial there is one automatically-timed dial change. The dial states in Task 2 trials are also pseudorandomly balanced, and the dial positions within those states are ordered in a pseudorandom sequence.

Figure 4A:
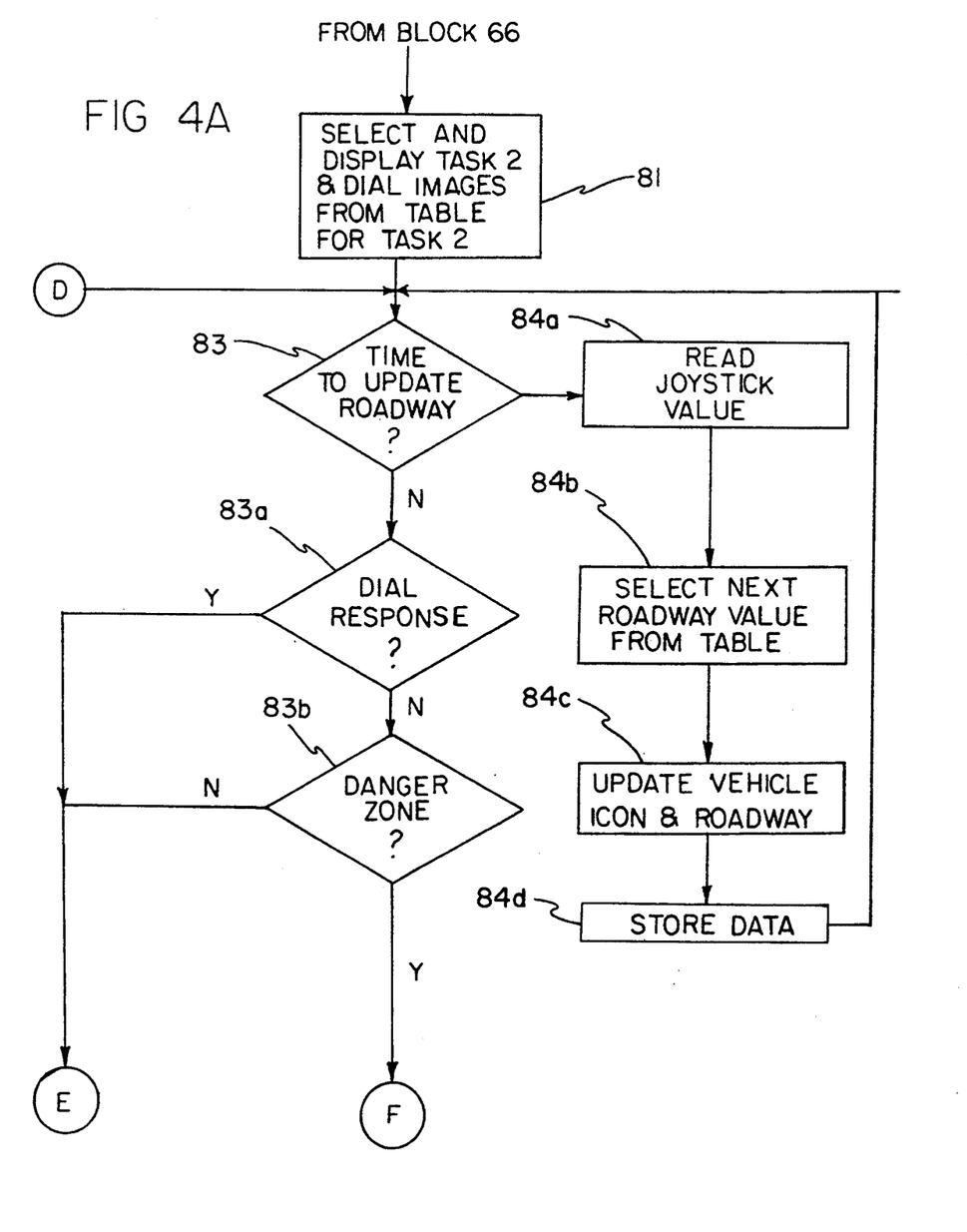
FIGS. 4A and 4B are flow charts of a routine for presenting a task requiring the use of a motor skill.
Figure 4B:
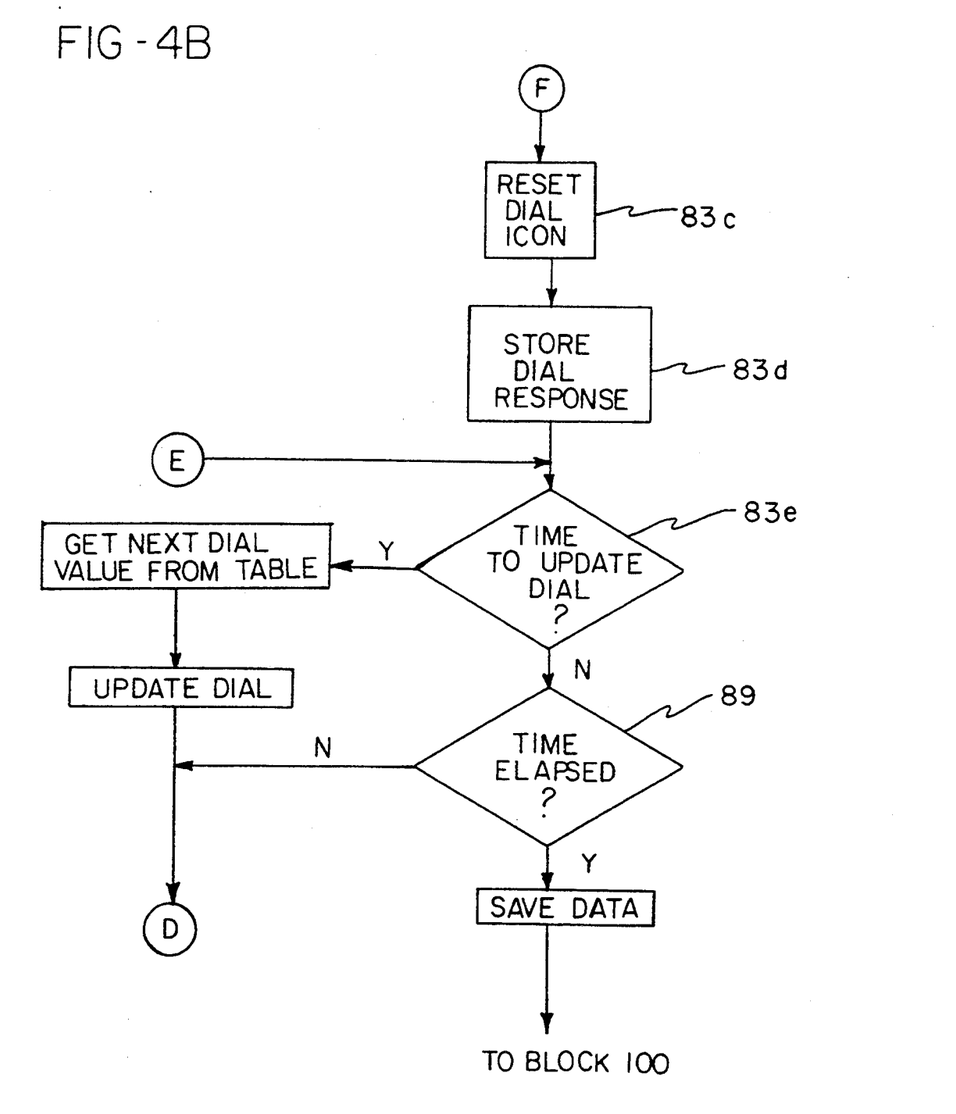
Figure 6:
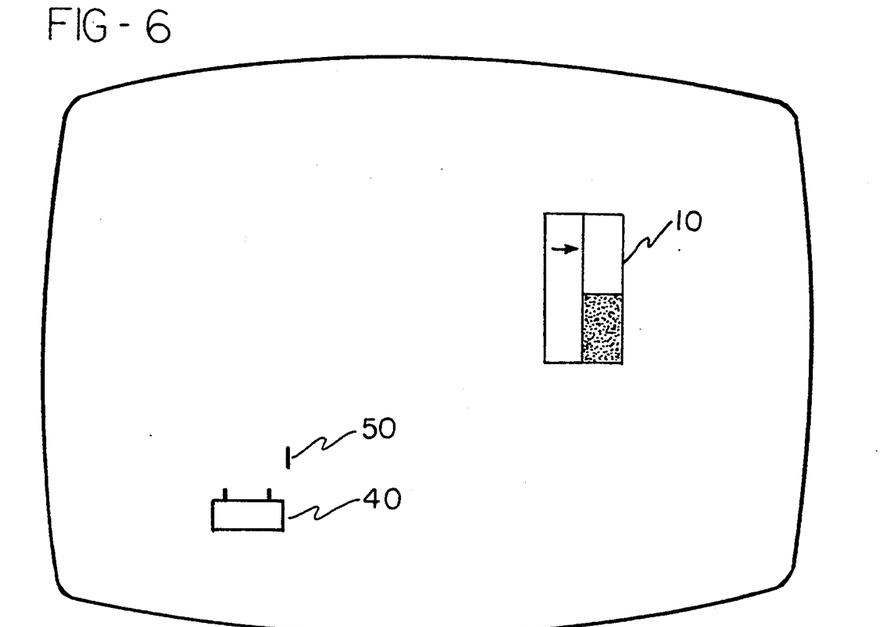
FIG. 6 is an illustration of a monitor display for a task requiring the use of a motor skill.

A flow chart for Task 2 is presented in FIGS. 4A and 4B. Whenever the tabulated sequence of task numbers calls for Task 2, the program causes the monitor to display a moving vehicle 40 and a roadway segment 50, as illustrated in FIG. 6 and indicated by block 81 of FIG. 4A. Again, the icon 10 appears in the upper right-hand corner of the display.

In a typical embodiment, Task 2 requires the operator to utilize his visual-motor skills to maintain the roadway within the boundaries of the extensions on the front of the vehicle. Joystick 21 is provided for that purpose. The lateral position of the road may be constructed as the sum of 5 sine waves, so as to provide an apparently random motion for the operator.

The roadway and joystick updates are performed every 33 msec (blocks 84a, 84b, and 84c) as a consequence of a check made at point 83 at FIG. 4A. This provides approximately 30 updates per second which is above the critical fusion frequency for most individuals at the intensity used and makes the movement of the roadway and vehicle appear smooth and continuous. After the update, the program stores the current relative position data (block 84d). This data is the signed difference between the screen position of the roadway and the position of the joystick as reflected by the position of the vehicle. These measurements are given in pixels. In the preferred version of the test, only every 4th data point is saved for later analysis. The system checks for an operator response at block 83a. Then a check is made at point 83b to determine whether the dial is in the danger zone. If not, the program records the inappropriate response and loops back to point 83a. In the event the dial is in the danger zone, then the dial is reset to the safe zone at block 83c. A record of the time of response is stored at block 83d and the program proceeds to point 83e.

Each performance of Task 2 continues for a fixed period of time, which may be the same as the maximum period of time allotted for any performance of Task 1. Thus, the program checks the elapsed time at point 89 and loops back to block 83 if time has not expired. The operator continues operating joy-stick 21 and pushbutton 15 (as required) while the program loops and collects data. When time finally expires the program proceeds to block 100 and increments the trial count.

A test conducted in accordance with this invention may test several individual skills as well as skill combinations. A task such as the above-described Task 1 exercises the mental function relating to visualization of objects. That skill is exercised simultaneously with a monitoring strategy and low-level psychomotor skill associated with the activation of switch 15 when indicator 13 of icon 10 enters Danger Zone 11. Task 2 tests a psychomotor skill requiring eye-hand coordination. That skill is also exercised simultaneously with the monitoring strategy and lower level psychomotor skill associated with the closure of switch 15.

The paradigm of the present invention is based upon the realization that a human operator may lose agility in switching resources even before he loses attention capacity. Thus, the new paradigm fractionates attention into several components and is more sensitive to performance degradation than prior art directed attention paradigms wherein attention in general is measured and changes in switching skills may be missed. In the preferred embodiment of the invention, as described above, the person never knows whether the next trial will switch. This forces the individual to attend, and prevents the automatic behavior which would make the test insensitive. In addition, a measure of the individual's ability to handle the infrequent or unexpected event may be obtained by reference to the trials in which the task does not switch. Thus, "surprise" and the person's ability to handle it are assessed. This ability, is one of the first things to become degraded in drug and alcohol use.

The added use of the danger indicating icon provides an assessment of the individual's multiplexing ability. Also, by comparing reaction times for trials where the danger zone was not entered against other trials where it was, it is possible to obtain a very refined measure of the attention allocation resource of the individual.

It will be appreciated that the test of the present invention may be tailored to the needs of a particular employer. Thus, skills other than those mentioned above could be exercised and/or switched and other types of operator control devices be used. In particular, the closure of switch 15 could be replaced by a keyboard entry. A left/right switch could be used for Task 1 responses, and a mouse or a paddle or other device could be used in place a joy-stick for the Task 2 performance function.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A method of measuring the ability of an operator to perform a job-related activity comprising the steps of:
   (1) presenting to said operator a plurality of occurrences of a first task requiring the utilization of a first skill associated with said activity;

(2) presenting to said operator a plurality of occurrences of a second task requiring utilization of a second skill which is different from said first skill and which is also associated with said activity;

(3) pseudorandomly controlling the sequence of presentation of said first and second tasks, so that said operator is forced to switch back and forth between said first and second skills without being able to anticipate the number of consecutive occurrences of said first task which will follow an occurrence of said second task; and (4) recording data indicating the success of said operator in performing said first and second tasks.

2. A method according to claim 1 wherein one of said tasks in a cognitive task involving mental processing of a plurality of different, cognitively relevant stimuli, each subject to occurrence in a plurality of different states; said method further comprising the step of displaying a balanced and pseudorandomly ordered presentation of all combinations of said stimuli and said states.

3. A method according to claim 1 and further comprising the step of presenting an attention shifting display to said operator during his performance of at least one of said first and second tasks.

4. A method according to claim 3 wherein said attention shifting step comprises the sub-steps of:

(1) creating a display of an icon which is selectively presentable between a range of safe conditions and a range of danger conditions, (2) providing said operator with danger response means for generating a danger response signal when one of said danger conditions is displayed, and (3) while said icon is being presented within said range of danger conditions, testing for a generation of said danger response signal by said operator and modifying said icon for presentation in a safe condition if said danger response signal is detected.

5. A method according to claim 4 wherein said attention shifting step is performed during both of said first and second tasks.

6. A method according to claim 5 wherein one of said first and second tasks requires said operator to utilize a cognitive skill and the other of said first and second tasks requires said operator to utilize a motor skill.

7. A method according to claim 6 further comprising the steps of generating a pseudorandom sequence of balanced numbers and using said sequence to control the presentation of at least one of said first and second tasks.

8. A method according to claim 6 wherein one of said first and second tasks requires said operator to utilize a skill associated with recognition of a spatial orientation and the other of said first and second tasks requires said operator to utilize a skill associated with eye-hand coordination.

9. Apparatus for testing the skill switching ability of a human operator comprising:

a monitor for displaying a graphical presentation to be observed by said human operator, graphics control means for causing said monitor to display an attention shifting icon and a sequential series of tasks, said series of tasks comprising tasks of a first type requiring said human operator to utilize a cognitive skill and tasks of a second type requiring said human operator to utilize a motor skill, attention response means for operation by said human operator to generate attention response signals related to a predetermined condition of said attention shifting icon, cognitive response means operable during the display by said monitor of tasks of said first type to receive cognitive responses from said human operator and generate corresponding cognitive response signals, motor response means operable during the display by said monitor of tasks of said second type to receive motor responses from said human operator and generate corresponding motor response signals, and computing means responsive to said attention response signals, said cognitive response signals and said motor response signals for computing a performance score for said human operator.

10. Apparatus according the claim 9 wherein said computing means and said graphics control means are combined within a common computer.

11. Apparatus according to claim 9 wherein said computing means comprises means for causing said monitor to display graphics for said series of tasks in a balanced pseudorandom sequence.

12. Apparatus according to claim 11 wherein said attention response means comprises a switch.

13. Apparatus according to claim 12 wherein said cognitive response means comprises a keyboard.

14. Apparatus according to claim 13 wherein said motor response means comprises a joy-stick.

15. A method of measuring the impairment of a human subject comprising the steps of conducting a performance test of said human subject as a base test, thereafter repeating said performance test, and comparing the results of the repeated performance test against the base test; said performance test comprising the steps of:

(1) presenting a cognitive task to said human subject;

(2) presenting a motor task to said human subject;

(3) forcing said human subject to perform said cognitive task and said motor task sequentially on a pseudorandomly alternating basis.

* * * * *

UNITED STATES PATENT AND TRADEMARK OFFICE
CERTIFICATE OF CORRECTION

PATENT NO. : 5,344,324
DATED : September 6, 1994
INVENTOR(S) : Robert D. O'Donnell & Samuel L. Moise, Jr.

It is certified that error appears in the above-indentified patent and that said Letters Patent is hereby corrected as shown below:

On the title page, item [56]: Other Publications

LOW COST, REAL TIME SIMULATION BASED ON IBM-PC COMPATIBLE COMPUTERS, by R. Wade Allen, Jeffrey R. Hogue, Anthony C. Stein, Ph.D., Bineal L. Aponso and Theodore J. Rosenthal, January 1989 (Presented at the Transportation Research Board Annual Meeting, Washington, D.C.)

Signed and Sealed this

Twenty-seventh Day of December, 1994

*Attest:*

BRUCE LEHMAN

*Attesting Officer*      *Commissioner of Patents and Trademarks*